United States Patent [19]

Goller et al.

[11] 4,174,338

[45] Nov. 13, 1979

[54] PASTY COMPOSITIONS FOR CROSSLINKING ORGANOPOLYSILOXANES TO SILICONE RUBBER

[75] Inventors: Heinz Goller, Bergisch-Gladbach; Hans-Hermann Schulz, Leichlingen; Bernhard Leusner, Leverkusen, all of Fed. Rep. of Germany

[73] Assignee: Bayer Aktiengesellschaft, Leverkusen, Fed. Rep. of Germany

[21] Appl. No.: 836,340

[22] Filed: Sep. 26, 1977

[30] Foreign Application Priority Data

Sep. 30, 1976 [DE] Fed. Rep. of Germany ....... 2644193

[51] Int. Cl.$^2$ ............................................. C08L 83/04
[52] U.S. Cl. .............................. 260/37 SB; 252/428; 252/431 C; 525/477
[58] Field of Search ........ 260/37 SB, 46.5 G, 46.5 R; 252/431 C, 428

[56] References Cited

U.S. PATENT DOCUMENTS

| | | | |
|---|---|---|---|
| 3,792,147 | 2/1974 | Wohlfarth et al. | 252/428 X |
| 3,850,971 | 11/1974 | Termin et al. | 260/46.5 R X |
| 3,957,683 | 5/1976 | Hittmair et al. | 252/431 C X |

FOREIGN PATENT DOCUMENTS

| | | | |
|---|---|---|---|
| 1153169 | 8/1963 | Fed. Rep. of Germany | 260/37 |
| 1669940 | 11/1970 | Fed. Rep. of Germany | 260/37 |
| 2313218 | 9/1974 | Fed. Rep. of Germany | 260/37 |

*Primary Examiner*—Lewis T. Jacobs
*Attorney, Agent, or Firm*—Sprung, Felfe, Horn, Lynch & Kramer

[57] ABSTRACT

A pasty composition for the room temperature crosslinking and curing of a vulcanizable organopolysiloxane, comprising a crosslinking agent for an organopolysiloxane, a curing catalyst therefor, and about 3–40% by weight of the total amount of the pasty composition of active hydrophilic silica as a thickener. The pasty composition may additionally contain up to about 40% by weight of at least one inactive filler. Advantageously, the organopolysiloxane is in one tube and the pasty composition is in another; lengths of material are squeezed out in easily ascertained proportions and are mixed in the presence of water, e.g. water vapor in the atmosphere, the mixture setting to a silicone rubber.

5 Claims, No Drawings

PASTY COMPOSITIONS FOR CROSSLINKING ORGANOPOLYSILOXANES TO SILICONE RUBBER

The invention relates to pasty compositions of mobile to solid, kneadable consistency, comprising essentially silicic acid esters, polysilicic acid esters or silane crosslinking agents, curing catalysts and active hydrophilic silicic acid as crosslinking components for silicone rubbers which are vulcanizable at room temperature on the basis of the silanol condensation.

It has been known for a considerable time to vulcanize silicone rubber mixtures, which comprise a hydroxyl-containing polyorganosiloxane as the polymer component, at room temperature by adding a silicic acid ester and a curing catalyst in the presence of water which is either added to the mixture or finds access to the mixture in the form of atmospheric moisture. These products are of great commercial importance, for example in mold construction, for potting, coatings and similar applications. They belong to the 2-component silicone rubbers which are vulcanizable at room temperature, since the component containing crosslinking agents and/or condensation catalyst is mixed with the second component, namely the polymer component, only shortly before use.

In the case of these 2-component silicone rubbers it has, for a considerable time, been desired that the component containing the crosslinking agent and curing catalyst should also be employed in a pasty consistency since this makes it possible, for example, by choosing the appropriate tube orifices, to obtain the quantitative ratios required for the 2-component composition by means of equal "lengths of ribbon" of polymer component and of crosslinking component, which offers more precise and simpler metering than the addition of a liquid second component and also permits simpler and better mixing of the two components.

There has hitherto been no lack of attempts to solve the problem of the manufacture and use of a pasty crosslinking agent technically and in an economically acceptable manner.

DT-AS (German Published Specification) No. 1,153,169 describes pasty 2-component silicone rubber mixtures. These comprise a polydimethylsiloxane with both ends terminated by hydroxyl groups, a crosslinking agent—which can be a hydrogenosilane-containing silicone or a silicic acid ester—and a filler. The second component contains a condensation catalyst, a diorganopolysiloxane with the ends terminated by triorganosiloxy groups, and likewise a filler. This composition has the disadvantage that the mixture which contains the vulcanizable polydiorganosiloxane with ends terminated by hydroxyl groups, and the crosslinking agent, suffers a noticeable loss, on storage, in its effectiveness as a crosslinking agent.

DT-OS (German Published Specification) No. 1,669,940 describes a process for the manufacture of elastomeric moldings, based on organopolysiloxanes, having a high tear-starting resistance and peel strength, which process comprises, inter alia, the use of pasty crosslinking agents, consisting of a dimethylsiloxane oil containing triorganosilyl groups, hydrogenated castor oil, a tin-containing condensation catalyst and solid calcium carbonate. However, this mixture has the disadvantage that calcium carbonate sediments on storage.

The use of hydrophobic, very finely divided silicon dioxide as a thickener for pasty crosslinking agents which in addition contain, as essential constituents, the crosslinking agent and the condensation catalyst, is described in DT-OS (German Published Specification) No. 2,313,218. Of course, this process makes it necessary to render the very finely divided silicon dioxide used hydrophobic, for example by treatment with organoalkoxysilanes or hexaorganodisilazanes, before use in the paste. In addition, the amount of filler, which has been rendered hydrophobic, that must be used is relatively large since the ability to assume the pasty consistency is of course diminished by the hydrophobic treatment.

The present invention relates to a pasty composition, containing crosslinking agents and curing catalysts, for organopolysiloxanes which are vulcanizable at room temperature, comprising essentially crosslinking agents, a curing catalyst and thickeners, characterized in that the thickener comprises about 3–40% by weight, relative to the total weight of the pasty composition, of active, hydrophilic silicic acid.

Surprisingly, it has been found that the described disadvantages of the state of the art, such as inadequate storage stability, sedimentation of the thickener or an additional hydrophobic treatment step do not arise, or are not essential, if hydrophilic active silicic acid, in the stated range of proportions, is added to a mixture of, essentially, silicic acid esters, polysilicic acid esters or silane crosslinking agents and curing catalyst.

Furthermore, up to 40% by weight (of the total mixture) of inactive filler can be added to the crosslinking paste containing hydrophilic active silica. Examples of inactive fillers are quartz powder, calcium carbonate, calcium silicate, calcined gypsum, titanium dioxide, diatomaceous earth, asbestos and pigments.

Crosslinking agents and curing agents can be activated before use by heating them together.

Further additives which can be used are inert substances conventionally employed for silicone rubber pastes, such as, for example, plasticizing polydimethylsiloxanes with terminal triorganosilyl groups, paraffin oils, paraffin greases—amongst these, especially "Vaseline ®"—castor oil and dyestuffs or pigments.

If the amount of hydrophilic active silicic acid added is kept below about 3%, the paste mixture is too soft unless further solid thickeners are added. If inactive fillers are also added, a sufficiently good pasty consistency can admittedly be obtained, but the excessive content of inactive filler, as compared to the proportion of active filler, causes a sediment to form on storage. If, when preparing the pastes, a proportion of about 40% of hydrophilic active silicic acid is exceeded, a paste consistency which permits good handling is no longer achievable.

The organopolysiloxanes employed are in the main polydiorganosiloxanes containing hydroxyl groups. These polydiorganosiloxanes can be substituted by any of the known monovalent hydrocarbon or halogenated hydrocarbon radicals, for example by alkyl radicals with 1–8 C atoms, such as methyl, ethy, propyl, butyl, pentyl, hexyl, heptyl and octyl, by alkenyl radicals with 1–8 C atoms, such as vinyl, allyl and butenyl, by halogenated alkyl radicals, such as chloropropyl and 3,3,3-trifluoropropyl, by cycloalkyl radicals, such as cyclobutyl, cyclopentyl and cyclohexyl, and also by aromatic radicals, such as phenyl, tolyl, xylyl and naphthyl, or by halogeno-aromatic radicals, such as chlorophenyl and chloronaphthyl, as well as by alkylaryl radicals, such as benzyl and phenylethyl.

In addition to the diorganosiloxy units ($R_2SiO$), the diorganopolysiloxanes can also contain triorganosiloxy units ($R_3SiO_{0.5}$), monoorganosiloxy units ($RSiO_{1.5}$) and unsubstituted silicon dioxide units ($SiO_2$).

Crosslinking substances which can be used are O-silicic acid esters, polysilicic acid esters or substituted silane crosslinking agents. Examples of O-silicic acid esters are O-silicic acid methyl, ethyl, n-propyl, isopropyl, chloroethyl, octyl, allyl, hexenyl, cyclohexyl, phenyl, benzyl and chlorophenyl ester, and mixed alkylated O-silicic acid esters, such as O-silicic acid dimethyl diethyl ester. Examples of the polysilicic acid esters formed by partial hydrolysis and condensation and/or by heating the abovementioned O-silicic acid esters are methyl, ethyl and n-propyl polysilicate.

Examples of silane crosslinking agents are methyltrimethoxysilane, methyltriethoxysilane, ethyltrimethoxysilane, ethyltriethoxysilane, n-propyltrimethoxysilane, n-propyltriethoxysilane, phenyltrimethoxysilane, phenyltriethoxysilane and methyltriacetoxysilane.

The amount of the crosslinking compound to be added is about 0.1 to 10 parts by weight per 100 parts by weight of polyorganosiloxane.

Curing catalysts which can be used in the process according to the invention are all catalysts which promote the silanol condensation, the reaction of silanol with alkoxy or other groups which are hydrolyzable by water, and the hydrolysis of silicon-bonded alkoxy or other groups.

Examples thereof are the metal salts of organic monocarboxylic acids which may contain lead, tin, zirconium, antimony, iron, cadmium, calcium, barium, manganese, bismuth or titanium as metals, such as dibutyl-tin dilaurate, dibutyltin diacetate, tin-II octoate, iron octoate, lead laurate, cobalt naphthenate, tetrabutyl titanate, tetraoctyl titanate and tetraisopropyl titanate. Further examples are amines such as n-hexylamine and cyclohexylamine, and amine salts such as hexylamine hydrochloride, butylamine acetate and guanidine diethylhexoate. Carboxylic acid salts of tin are preferred as catalysts. The amount of curing catalyst added is between 0.1 10%, based on the organopolysiloxane employed.

The hydrophilic active silicon dioxide employed as the solid thickener has a surface area, by the BET method, of about 35-600 $m^2/g$, preferably about 40 to 300 $m^2/g$. The silicon dioxide can be manufactured as an "aerogel" by combustion of silanes, for example of silicon tetrachloride or trichlorosilane, in the gas phase. These aerogels are commercially available; they are offered, for example, under the name "Aerosil ®" or "Cabosil ®". In addition to pyrogenically manufactured active hydrophilic silicon dioxide, it is also possible to employ, according to the invention, fillers which are manufactured by dehydrating silicic acid hydrogels or by precipitating aqueous silicic acid solution.

The crosslinking agent paste which, according to the invention, consists of silicic acid, polysilicic acid or silane crosslinking agents, curing catalysts, hydrophilic active silicic acids and, optionally, other constituents, such as, for example, oily or waxy paraffins such as, for example, "Vaseline ®", can be produced by mixing the components, for example in a kneader. A simple process for handling this crosslinking agent paste when carrying out the vulcanization is provided by filling both the crosslinking agent paste and the polymer paste into separate tubes and choosing the diameters of the tube orifices so that in each case equal "ribbon lengths" of the pastes pressed out of the tubes can be measured out. Per 100 parts of polymer paste, between about 3 and 40 parts by weight of crosslinking agent paste are used.

The pasty crosslinking agents according to the invention can be employed, together with polymer mixtures, comprising hydroxyl-containing polyorganosiloxanes and other constituents, in all cases where two-component silicone rubbers are used, for example in moldmaking. Dental impressions is the preferred field of use.

The present invention will be explained in further detail with the aid of the examples which follow:

EXAMPLE 1

200 g of Vaseline (paraffin grease) 40 g of Aerosil 130 (pyrogenic silicic acid from Messrs. Deutsche Gold- und Silberscheideanstalt, vorm. Roessler, Frankfurt/M., West Germany, having a specific surface area, by the BET method, of $130\pm25$ $m^2/g$), 88 g of hexamethoxydisiloxane and 72 g of dibutyl-tin dilaurate are introduced, in the stated sequence, into a laboratory kneader of 0.75 l capacity, equipped with Sigma blades. The composition is mixed for 3 hours at room temperature, with exclusion of moisture. Advantageously, the paste obtained is immediately filled into tubes.

EXAMPLE 2

300 g of tetraethoxysilane and 300 g of dibutyl-tin dilaurate are stirred at 120° C. in a 1 l flask equipped with a stirrer and a nitrogen connection. 140 g of Vaseline, 40 g of Aerosil 130, 40 g of Sikron 6000 (quartz powder from Quarzwerke GmbH, 5020 Frechen, West Germany) and 180 g of the above crosslinking agent/curing agent mixture are introduced, in the stated sequence, into the laboratory kneader of Example 1. Thereafter the further procedure is as described under Example 1.

EXAMPLE 3.

A paste is produced, as described under Example 1, from 140 g of Vaseline, 84 g of Aerosil OX 50 (pyrogenic silica from Messrs. Deutsche Gold- und Silberscheideanstalt, vorm. Roessler, having a specific surface area, by the BET method, of $50\pm15$ $m^2/g$), 8 g of titanium dioxide and 168 g of the crosslinking agent/curing agent mixture from Example 2.

EXAMPLE 4 (comparative example)

100 g of Vaseline, 164 g of Aerosil OX 50, 8 g of titanium dioxide and 128 g of the crosslinking agent/curing agent mixture from Example 2 are introduced into the laboratory kneader of Example 1 and mixed for 3 hours at room temperature. The resulting composition is very viscous.

EXAMPLE 5

180 g of a polydimethylsiloxane, with terminal hydroxyl groups, having a viscosity of 800 cP, and 170 g of a polydimethylsiloxane, with terminal hydroxyl groups, having a viscosity of 22,000 cP are heated to 100° C. in a 3 l thick-walled glass cylinder with a metal stirrer.

60 g of Sikron 6000 quartz powder are next added, while stirring, the mixture is stirred for 10 minutes and 590 g of calcined gypsum are then added gradually. The mixture is then stirred for a further hour at 100° C. and for a further two hours without supplying heat.

EXAMPLE 6

Polydimethylsiloxanes with terminal hydroxyl groups, namely 700 g of a material of viscosity 1,000 cP and 300 g of a material of viscosity 2,000 cP, 150 g of calcium silicate and 50 g of calcined gypsum are brought together in a 2 l thickwalled glass cylinder with a metal stirrer, and are stirred for two hours.

EXAMPLES 7–11 (vulcanizations)

10 g portions of the polymer mixture according to Example 5 or 6 are intimately mixed with up to 2 g of crosslinking agent paste according to Examples 1–4. One part is transferred, after one minute, into a small metal cap; the top is wiped over to give a smooth surface and the metal cap, containing the vulcanization mixture, is introduced into a thermostat containing water at 37° C. The hardness of the vulcanized samples, in Shore A, is in each case measured after 4'30", 6', 8' and 10', both when using the crosslinking paste immediately after its preparation, and when using it after it has been stored.

The processing behavior is tested, using another portion of the mixture of polymer mixture and crosslinking agent paste, by carrying out the so-called "digital test". For this purpose, a part of the mixture is taken between the thumb and the index finger and these digits are moved relative to one another until the vulcanization mixture "tears". The time from starting the mixing to "tearing" represents the digital test.

The table which follows contains vulcanization results of mixtures which were determined immediately after preparation of the crosslinking agent paste, and after 12 months' storage of the paste.

Table

| Ex. No. | Cross-linking agent from Example No. | Amount of crosslinking agent in g | Polymer from Example No. | Digital Test immediate | Digital Test after 12 months | Shore A after 4 minutes 30 seconds immediate | Shore A after 4 minutes 30 seconds after 12 months | Shore A after 6' immediate | Shore A after 6' after 12 months | Shore A after 8' immediate | Shore A after 8' after 12 months | Shore A after 10' immediate | Shore A after 10' after 12 months |
|---|---|---|---|---|---|---|---|---|---|---|---|---|---|
| 7  | 1 | 1   | 5 | 2'45" | 2'42" | 9  | 11 | 17 | 17 | 24 | 23 | 27 | 28 |
| 8  | 2 | 0.8 | 5 | 2'35" | 2'38" | 18 | 17 | 26 | 24 | 32 | 30 | 34 | 33 |
| 9  | 3 | 1   | 5 | 2'35" | 2'33" | 20 | 20 | 25 | 24 | 27 | 26 | 29 | 28 |
| 10 | 3 | 2   | 6 | 2'45" | 2'40" | 32 | 32 | 41 | 41 | 44 | 45 | 47 | 48 |
| 11 | 4 | 1   | 5 | 5'    | 5'    | 0  | 0  | 4  | 6  | 22 | 23 | 29 | 26 |

It will be appreciated that the instant specification and examples are set forth by way of illustration and not limitation, and that various modifications and changes may be made without departing from the spirit and scope of the present invention.

What is claimed is:

1. A pasty composition for the room temperature crosslinking and curing of a vulcanizable organopolysiloxane, comprising a crosslinking agent for an organopolysiloxane, a curing catalyst therefor, and about 3–40% by weight of the total amount of the pasty composition of active hydrophilic silicic acid as a thickener.

2. A composition according to claim 1, additionally containing up to about 40% by weight of at least one inactive filler.

3. A composition according to claim 1, wherein the silicic acid comprises about 20% by weight.

4. In the production of a crosslinked and cured silicone rubber by mixing a vulcanizable organopolysiloxane with a crosslinking agent and a curing catalyst therefor in the presence of water, the improvement which comprises employing the crosslinking agent and the curing catalyst in the form of a pasty composition according to claim 1.

5. The process according to claim 4, wherein the pasty composition contains up to about 40% by weight of at least one inactive filler.